United States Patent
Heller (10) Patent No.: US 12,203,814 B2
(45) Date of Patent: *Jan. 21, 2025

(54) SYSTEMS AND METHODS FOR ACCURATE DETECTION OF FEBRILE CONDITIONS WITH VARYING BASELINE TEMPERATURES

(71) Applicant: Wello, Inc., Addison, TX (US)

(72) Inventor: Alan C. Heller, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/400,744

(22) Filed: Aug. 12, 2021

(65) Prior Publication Data

US 2023/0050433 A1    Feb. 16, 2023
US 2024/0240996 A9    Jul. 18, 2024

Related U.S. Application Data

(63) Continuation-in-part of application No. 15/604,792, filed on May 25, 2017.

(51) Int. Cl.
*G01K 13/20* (2021.01)
*A61B 5/00* (2006.01)
(Continued)

(52) U.S. Cl.
CPC .......... *G01K 13/223* (2021.01); *A61B 5/0008* (2013.01); *A61B 5/01* (2013.01);
(Continued)

(58) Field of Classification Search
CPC ...... G01K 13/223; A61B 5/0008; A61B 5/01; A61B 2562/0271; B65C 11/02;
(Continued)

(56) References Cited

U.S. PATENT DOCUMENTS

2016/0117813 A1* 4/2016 Gross .................... G16H 40/67
                                                     600/479
2017/0258335 A1* 9/2017 Heller .................... A61B 5/015
(Continued)

FOREIGN PATENT DOCUMENTS

CN        111521268      * 7/2021    .......... G01K 13/223
WO    WO 2018057672      * 3/2018
(Continued)

OTHER PUBLICATIONS

English language translation of CN 111521268, generated Mar. 28, 2022 by Clarivate Analytics.*
(Continued)

*Primary Examiner* — Alexei Bykhovski (57) ABSTRACT

The present invention is directed to systems and process for detecting a febrile condition in screening of multiple or large groups of persons for the likelihood of infectious diseases. The system comprises a temperature measurement device having at least a processor, a display, temperature sensor, camera module, and facial recognition software. The display may include a positional overlay. The system further includes a database containing baseline temperatures for a number of persons, including baseline temperatures by age group and by gender. An input device optionally may identify the specific person or provide survey questions to a person to further determine a febrile condition. Based on the baseline temperatures, measured temperature and other characteristics of the person, a febrile condition may be determined. Additionally, the system may include a secondary screening component providing nasal swabbing or saliva testing.

16 Claims, 7 Drawing Sheets

(51) Int. Cl.
  *A61B 5/01* (2006.01)
  *B65C 11/02* (2006.01)
  *G06F 3/0488* (2022.01)
  *G06K 9/00* (2022.01)
  *G06V 40/16* (2022.01)
  *G06V 40/60* (2022.01)
  *G01J 5/00* (2022.01)

(52) U.S. Cl.
  CPC .......... *B65C 11/02* (2013.01); *B65C 11/0289* (2013.01); *G06F 3/0488* (2013.01); *G06V 40/172* (2022.01); *G06V 40/67* (2022.01); *A61B 2562/0271* (2013.01); *G01J 5/00* (2013.01); *G06V 40/178* (2022.01)

(58) Field of Classification Search
  CPC . B65C 11/0289; G06F 3/0488; G06V 40/172; G06V 40/67; G06V 40/178
  See application file for complete search history.

(56) References Cited

U.S. PATENT DOCUMENTS

| | | | | |
|---|---|---|---|---|
| 2019/0028690 | A1* | 1/2019 | Raghoebardajal ... | H04N 13/371 |
| 2020/0286600 | A1* | 9/2020 | De Brouwer .......... | G16H 50/20 |
| 2020/0366671 | A1* | 11/2020 | Larson .................. | H04W 12/06 |
| 2020/0394391 | A1* | 12/2020 | Zhang .................. | G06V 40/171 |
| 2021/0294104 | A1* | 9/2021 | Hossain ............. | G02B 27/0093 |
| 2021/0366607 | A1* | 11/2021 | Kolluri .................. | G16H 10/65 |
| 2022/0036395 | A1* | 2/2022 | Huang ................. | G01K 13/223 |

FOREIGN PATENT DOCUMENTS

| | | | | |
|---|---|---|---|---|
| WO | WO2019027503 | * | 2/2019 | ............ G06V 40/16 |
| WO | WO 2022014026 | * | 1/2022 | ........... G01K 13/223 |

OTHER PUBLICATIONS

English language translation of WO 2022014026, generated Mar. 28, 2022 by Clarivate Analytics.*
English translation of WO 2022/014026 provided by USPTO machine translation services. Accessed Sep. 21, 2022.*
McCallum, K. "4 Questions You May Have About COVID-19 Testing, Answered." Houston Methodist <https://www.houstonmethodist.org/blog/articles/2020/jul/4-questions-you-may-have-about-covid19-testing-answered/> Published Jul. 14, 2020; accessed Sep. 21, 2022.*
Waalen et al (Is Older Colder or Colder Older? The Association of Age With Body Temperature in 18,630 Individuals, J Gerontol A Biol Sci Med Sci. May 2011;66A(5):487-492) (Year: 2011).*

* cited by examiner

SYSTEMS AND METHODS FOR ACCURATE DETECTION OF FEBRILE CONDITIONS WITH VARYING BASELINE TEMPERATURES

BACKGROUND

Cross-Reference to Related Applications

The present invention is related to those disclosed in the following U.S. Provisional and Non-Provisional Patent Applications, which are commonly owned and assigned with the present application and which is hereby incorporated by reference for all purposes:
1) Ser. No. 13/161,771 filed Jun. 16, 2011, entitled "System for Detecting a Febrile Condition and Reducing the Risks of Spreading Infection," now U.S. Pat. No. 8,593,251.
2) Ser. No. 13/685,574 filed Nov. 26, 2021, entitled "System and Process for Detecting a Febrile Condition," now U.S. Pat. No. 8,686,863.
3) Ser. No. 14/056,433 filed Oct. 21, 2013, entitled "Systems and Devices for Real Time Health Status Credentialing," now U.S. Pat. No. 9,618,401.
4) Ser. No. 15/604,792, filed on May 25, 2017, entitled "Systems for Real Time Febrility Detection and Notification."

FIELD OF THE INVENTION

The technology relates to systems and methods for use in screening of multiple or large groups of persons for likelihood of infectious diseases, and more particularly, this technology relates to rapidly screening persons in certain monitored facilities without exposure to employees or healthcare workers by obtaining, accumulating, and processing temperature data in view of potentially varying baseline temperatures for differing persons to more accurately determine if a specific person is exhibiting a temperature indicating an actual or potential febrile condition.

DESCRIPTION OF THE RELATED ART

Due to numerous recent contagious diseases, there is an increasing need to screen and identify individuals that may be infected with a contagious disease. For certain infectious diseases, the risk is high that an infected individual may transmit the disease to others within the same location.

For example, diseases such as the seasonal flu are easily spread from person to person each season. Based on a 2018 Centers for Disease Control (CDC) study published in Clinical Infectious Diseases, it was determined that, on average, about 8% of the U.S. population gets sick each season. Healthy adults may be able to infect others up to 5 to 7 days after their sickness is detected. One of the early detectable signs of certain infections is the existence of a febrile condition or fever. These sick adults are also able to infect others before they recognize their own febrile condition. As such, febrile condition detection is vital to identifying, isolating and preventing individuals who are infected from being in areas with healthy persons and potentially infecting those healthy persons.

According to epidemiologists, approximately 80% of all infections originate from a super-spreader. In our study in a Mississippi hospital, 90% of patients admitted for flu had temperatures under 100.4 F, the CDC's lower limit. Specifically, in the sick clinic 90% of all patient temperatures recorded over 99.1 F were temperatures which were still under 100.4 F. Conversely, in a physical therapy clinic housing non-sick patients nearby, only 1/300 people were recorded with a temperature above 99.1 F. This further supports the conclusion that baseline temperatures other that 100.4 F should be considered to more accurately determine a potential febrile condition.

The increased contagiousness of the COVID-19 virus and its numerous variants exacerbated the need for febrile detection. Unlike the flu, for COVID-19, the CDC says it is possible for people to spread the virus for about 2 days before experiencing signs or symptoms and remain contagious for at least 10 days after signs or symptoms first appeared. If someone is asymptomatic or their symptoms go away, it is possible to remain contagious for at least 10 days after testing positive for COVID-19. While COVID-19 and flu viruses are thought to spread in similar ways, COVID-19 is more contagious among certain populations and age groups than flu. Also, COVID-19 has been observed to have more superspreading events than flu. This means the virus that causes COVID-19 can quickly and easily spread to numerous people and result in continuous spreading among people as time progresses.

As mentioned supra, one of the recognized methods of identifying an individual with an infectious disease such as the flu or COVID-19 is to determine whether a person has a febrile condition. This is often also the earliest sign of the infection. Accordingly, measuring and monitoring for a febrile condition in facilities such as mass transit stations, airports, workplaces, hotels, hospitals, schools, and other places where large numbers of people congregate or interact increases the likelihood of identifying and isolating potentially infected persons and preventing or reducing the risk of transmission of the infection. Many types of thermometers have been developed to measure body temperature without having the need to contact the potentially infected person. For example, infrared thermometers (IRT) are fast, convenient and easy to use. Two types of infrared thermometers are typically used to measure body temperature: tympanic and forehead. With the spread of COVID-19 coronavirus, forehead temperature measurement eliminates physical contact and is widely used to screen people for a febrile condition and measurement studies showed that these infrared thermometers provide adequate to good precision.

Additionally, other symptoms of COVID-19 or other infectious diseases may include hypoxia. While COVID-19 often includes respiratory issues, some patients with COVID-19 may have significantly reduced pulse oximetry readings (e.g., hypoxia) without signs of respiratory distress. However, certain side effects of hypoxia can be detected from changes or signs in facial characteristics.

With respect to the detection of a febrile condition, the CDC considers a person to have a fever when he or she has a measured temperature of 100.4° F. (38° C.) or greater, or feels warm to the touch, or gives a history of feeling feverish. However, as discussed in more detail herein, these tests lead to missing 90% of elevated temperatures.

Likewise, 42 Code of Federal Regulations parts 70/71 Final defines an ill person as someone who: 1. Has a fever (has a measured temperature of 100.4° F. [38° C.] or greater, or feels warm to the touch, or gives a history of feeling feverish) accompanied by one or more of the following
  skin rash
  difficulty breathing
  persistent cough
  decreased consciousness or confusion of recent onset new unexplained bruising or bleeding (without previous injury)

persistent diarrhea persistent vomiting (other than air sickness)

headache with stiff neck, or appears obviously unwell; OR has a fever that has persisted for more than 48 hours.

Using this CDC baseline temperature, a standard thermal detection kiosk used in the field considers a person as likely to not have a febrile condition if the person's measured temperature is below the set CDC guidelines or some other preset value. However, this system and methodology is flawed as it does not fully account for varying baseline temperatures of different age groups, gender, ethnicities, times of days, outlier individuals or any other factors that change the baseline temperatures from person to person.

Additionally, measuring and processing temperature to detect for a fever and monitoring for a fever in facilities where large numbers of people congregate requires speed and efficiency, but it needs to be accomplished without sacrificing accuracy. For certain contagious diseases, including COVID-19, the rate of infections in certain localized areas may be such as low as 1 out of 100 or 1 out of 1000. Due to this lower infected population rate in certain localized areas, numerous operators of non-FDA cleared thermal detection kiosks tend to set fever baseline temperatures for detection towards higher temperatures to avoid false positives, rather than ensuring optimal detection. The reason being that a false positive may delay activities within the facility.

For example, in mass transit locations such as Love Field airport in Dallas, Texas, the airport screened over 100,000 passengers in 2020 using thermal kiosks but identified no person having a febrile condition. Although this result indicates that 0 false positives in passengers or other persons were detected, and no passengers were detained, or denied access to the facility, this result is likely flawed. Based on average local infection data, potentially approximately 500 passengers or other persons who might have had a febrile condition were admitted into the facility. Because of the kiosk's baseline temperature settings and other conditions, passengers or other persons may have had a false negative detected but was nonetheless admitted to the facility despite likely having a febrile condition. For example, U.S. Pat. No. 8,593,251, which is incorporated by reference in its entirety, discloses systems for detecting a febrile condition and reducing risks of spreading infection including taking action to restrict or deny ingress based on the determined febrile condition of the person.

Nonetheless, in these situations where the operators of the thermal kiosks were willing to accept false negatives (e.g., allowing access to persons with a febrile condition) but avoid false positives, this creates a potentially dangerous situation where potentially infectious individuals having a febrile condition were allowed entry due to improper configuration and inaccurate baseline temperature determinations present in a thermal kiosk intended to control entry.

As such, there exists a need for systems and methods to more accurately determining febrile conditions in different persons who may have varied and different baseline temperatures. To do so, identification of each person, or characteristics of that person, is necessary to compare with the proper baseline temperature for that person. Furthermore, there exists a need for a system to mass detect certain febrile conditions rapidly and more accurately without exposure to employees of a monitored zone.

As such, there also exists a need for systems and methods which provide for fast and accurate screening to reduce or eliminate false negatives while secondarily eliminate all false positives.

Additionally, there exists a need to combine multiple screening methods while economizing the time of the screened person. For example, temperature screening may be combined with hypoxia detection to provide greater accuracy. For example, temperature screening may be combined with a survey screening that allows for self-assessment of a person's current condition to provide greater accuracy. As another example, temperature screening may be combined with a rapid test such as a nasal swab or saliva test to provide greater accuracy.

SUMMARY OF THE INVENTION

The present invention is directed to systems and processes for detecting a febrile condition, especially in highly trafficked areas. The system comprises non-volatile memory storing baseline temperatures, a camera module for capturing the image of a user and operable with facial recognition software stored on the non-volatile memory, a display screen, an input device for permitting the user to input information related to a user's health, a wireless temperature sensor configured to measure the temperature of the user, and a processor configured to compare the measured temperature of the user with a stored baseline temperature.

Additionally, the present invention may include a positional overlay for instructing the correct position for the user to optimally measure a temperature.

Additionally, the present invention may include an RFID reader or login to specifically identify the user such that the processor compares the measured temperature with a stored baseline temperature specific to the user.

Alternate embodiments of the system comprise non-volatile memory storing baseline temperatures, a camera module for capturing the image of a user operable with facial recognition software stored on the non-volatile memory, a display screen, an input device for permitting the user to input information related to a user's health, a wireless temperature sensor configured to measure the temperature of the user, and a processor configured to operate with the facial recognition software to determine at least one of a user age or user gender, and the processor configured to compare the measured temperature of the user with a stored baseline temperature associated with at least one of a user age or user gender.

These and other features, aspects, and advantages of the invention will become better understood with reference to the following description, and accompanying drawings.

DETAILED DESCRIPTION

While the inventions disclosed herein are susceptible to various modifications and alternative forms, specific embodiments are shown by way of examples in the drawings and described in detail. It should be understood that the figures and detailed description discussed herein are not intended to limit the invention to the particular forms disclosed. On the contrary, the intention is to cover all modifications, equivalents and alternatives falling within the spirit and scope of the present inventions as defined by the appended claims. Description will now be given of the invention with reference to FIGS. 1-6.

As a preliminary matter, there are several factors that may, or ought, to be taken into account in making a determination about whether a person is exhibiting a febrile condition. One of the easily measured factors is a person's thermal temperature as measured by an infrared sensor. However, according to the research related to the present invention, core body temperature (Tc) varies from one person to another, as well as varies from one age group to another, as well as for different genders, and when measured at different times of days. Therefore, Tc is not constant for all persons, although 98.6 F is regarded as "normal" (i.e., not febrile). And the CDC considers a person to have a fever when he or she has a measured temperature of at greater 100.4° F. However, as taught herein, a more accurate determination whether a person has a febrile condition is to accumulate a database of that specific person's temperature over a period of time and to obtain a baseline or cluster of Tc from that accumulated data for that specific person. However, in situations where mass detection is necessary, a person may not have a database of their specific baseline temperatures to compare to. As such, accuracy can be increased by comparing an unknown or unidentified person with baseline temperatures according to that person's age range, gender, etc. Furthermore, even the time of the day a person is measured may affect the person's temperature. Therefore, the comparison between the baseline temperature and a measured temperature may be adjusted to compensate for different baseline temperature for different times of day as peoples' temperature tend to be lower in the morning and higher in the evenings. Additionally, to further increase accuracy, the measured temperature may be adjusted to compensate for differences in the ambient temperature.

Figure 1:
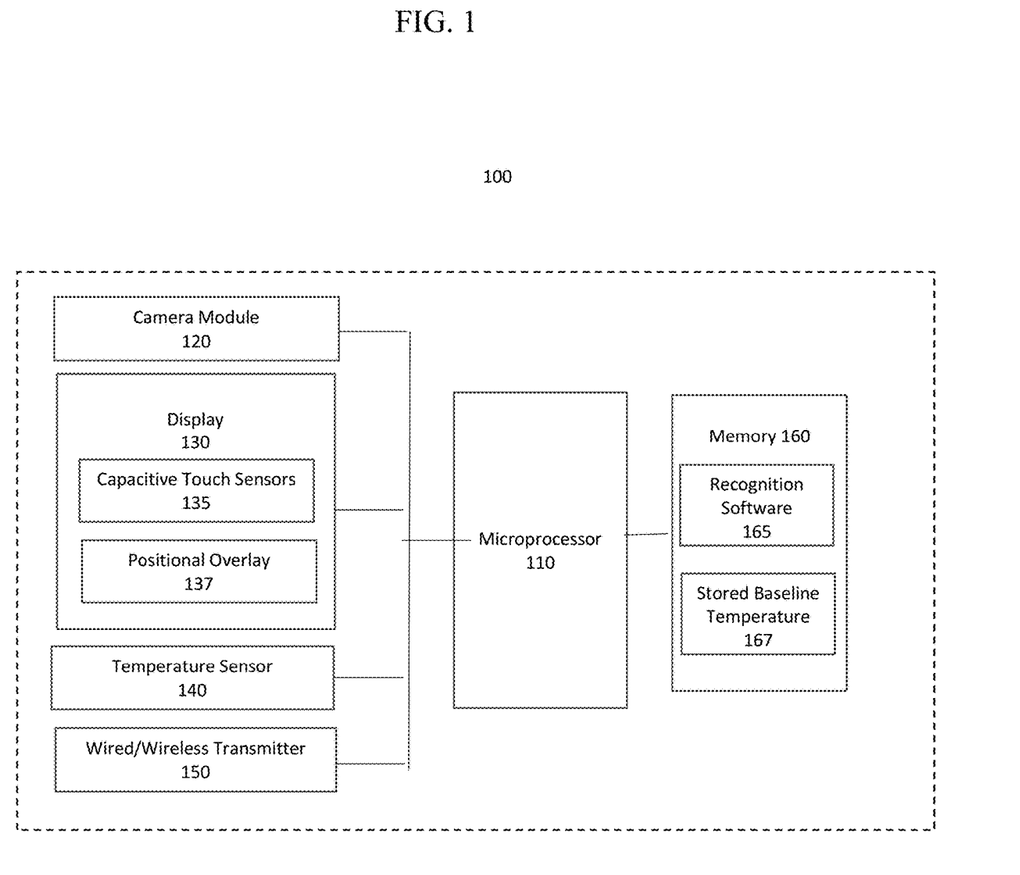
FIG. 1 is a block diagram of the novel combination of components of an exemplary embodiment of a kiosk system in accordance with the present invention.

Referring now to FIG. 1, the primary temperature monitor 100 includes microprocessor 110 and memory 160. Memory 160 may include both volatile and non-volatile memory. In the exemplary embodiment, memory 160 includes facial recognition software 165 and a database 167 which stores baseline temperatures for known persons, age ranges, genders, times of data, or any other baseline temperatures in accordance with the present invention. Although FIG. 1 depicts the database 167 as stored onboard local memory 160, the database 167 may also be stored remotely from temperature monitor 100 on a local network or a remote server. In an alternate embodiment, the facial recognition software 165 or the baseline temperature comparison software may be stored remotely from the temperature monitor on a local network or a remote server to offload processing power.

Temperature monitor 100 preferably includes a camera module 120 for capturing an image of a person's face so as to play back to the person on display 130. The display 130, along with the microprocessor 110 and software 165, ideally projects a positional overlay 137 onto the display 130 thereby indicating to the person the optimal position for both facial recognition and for detection by the temperature sensor 140 of the monitor 100 to obtain the person's Tc. For example, positional overlay 137 may instruct the person to move further or closer away until the entirety of the person's face is within the positional overlay 137.

The temperature sensor 140 may be infrared and optimally obtains a temperature reading from the person's forehead. Although scanning other areas of the of the person's person's body may also be applicable, scanning the forehead typically results in a more rapid continuous scanning. The temperature monitor 100 further includes a transmitter 150 to transmit to a remote server the obtained temperature readings and associated data such as the ambient temperature, person's age range, gender, and/or the time of the day the reading was taken. The transmission of the temperature along with the additional associated data helps improve the accuracy of the baseline of persons in various group by aggregating data from multiple kiosks resulting in more comprehensive sample sizes.

Additionally, the camera module 120, along with the microprocessor 110, and facial recognition software 165 are used in conjunction to identify the person if the person is a known person or to classify the person by age and/or gender if the person is an unknown person. To accomplish this, camera module 120, equipped to zero in on facial features, focuses on the facial features of the person and compares facial recognition image data with the database stored in memory or sends the facial recognition image data to a server that includes a database having facial recognition data of known persons. For a known person, using the facial recognition image data, microprocessor 110 along with software 165 determines the identity of the known person, which may be used to provide stored baseline temperature information for the known person. For an unknown person, using the facial recognition image data, microprocessor 110 along with software 165, calculates an approximate age for the person and/or identifies the likely sex of the person, which may be used to provide stored baseline temperature for the approximate age and sex.

In an alternate embodiment, microprocessor 110 and facial recognition software 165 scans the face of the person for signs of hypoxia. Such signs of hypoxia include changes in the color of the skin.

The display 130 may further include resistive, capacitive, or any other touch sensors 135 to allow the person to enter his or her information as well as provide responses to a survey or screening questions. Such survey or screening questions may include whether or not the person feels sick, whether or not the person has been exposed to sick individuals within a certain time period, and/or whether or not the person has traveled to certain known regions of infection hotspots.

In an alternate embodiment, the kiosk may further include a testing kit. A testing kit may be one of a saliva-based test, nasal swab, or any other acceptable rapid test. In a situation when the kiosk determines a likely febrile condition, the test kit may be unlocked and presented to a person such that a secondary testing can be performed to ensure the elimination of false negatives or false positives.

Figure 2:
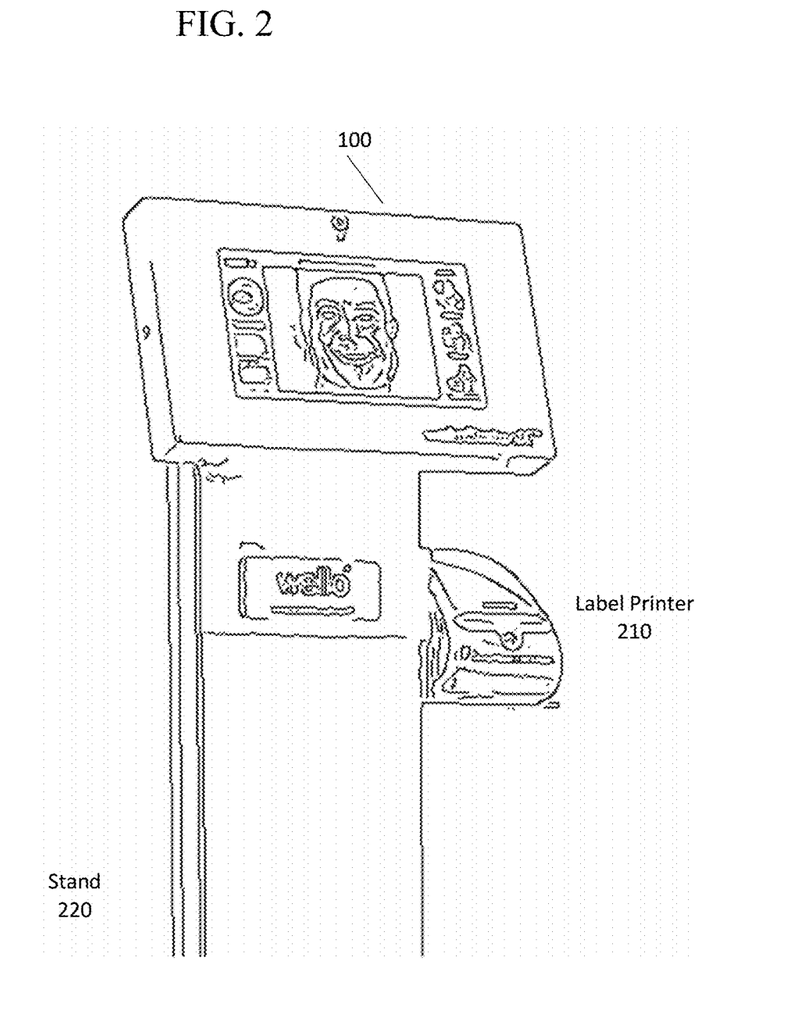
FIG. 2 depicts a perspective view of an exemplary embodiment of the invention as it may exist in operation.

Referring to FIG. 2, where an exemplary kiosk containing the temperature monitor 100 is depicted. When placed at a point of ingress, such as an office building, an exemplary kiosk may further include a label printer 210. Once the temperature monitor 100 determines whether or not a person has a febrile condition or is likely to have febrile condition, the label printer 210 subsequently prints an ID or access badge which grants or denies access. To optimize scanning efficiency, an exemplary kiosk further includes an adjustable height stand 220. The exemplary kiosk is typically placed in a place of ingress to a location or event and to expedite monitoring of multiple persons attempting to enter, and the temperature monitor is typically placed at or near eye level such that only minimal guidance is needed from the positional overlay 137.

Figure 3:
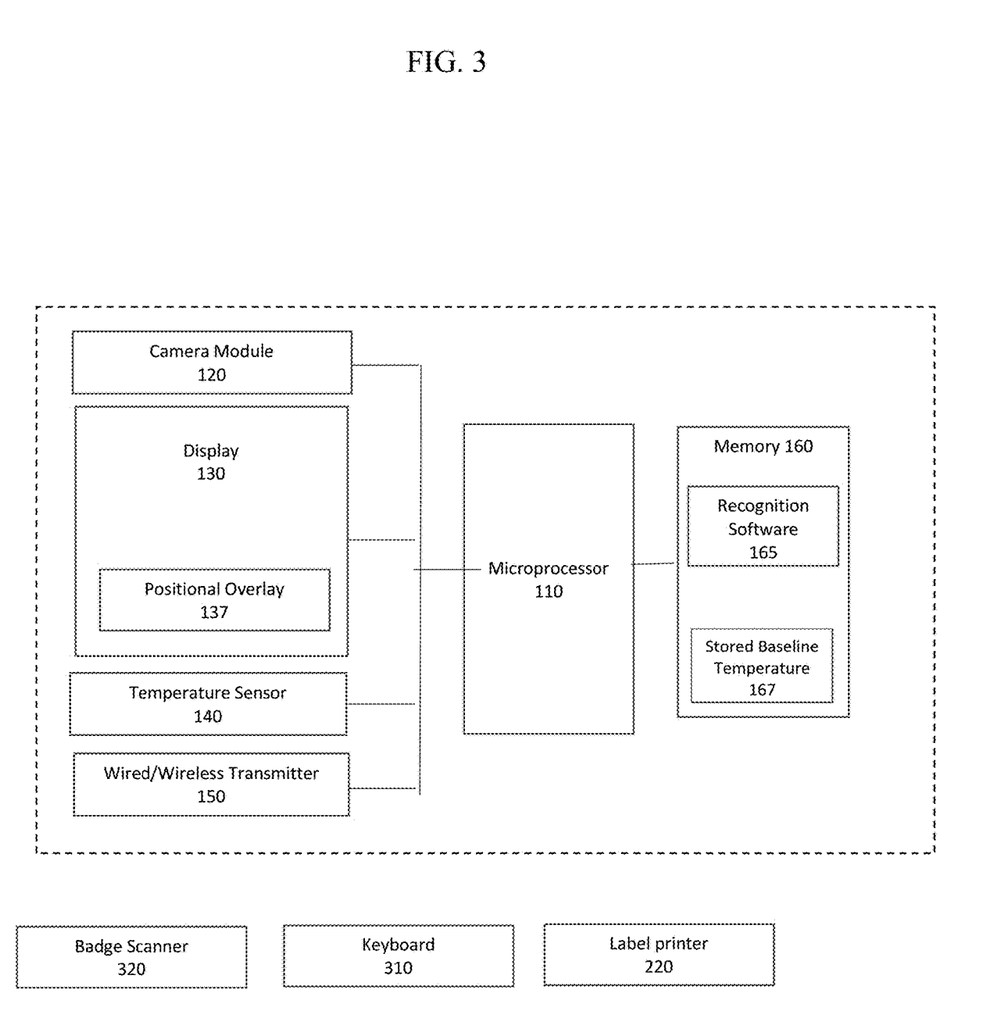
FIG. 3 is a block diagram of the novel combination of components of an alternate exemplary embodiment of a kiosk system in accordance with the present invention.

Referring to FIG. 3, an alternate embodiment of the temperature monitor 100 is depicted. In certain work environments, where information regarding each employee has been recorded, such as their age, sex, and/or known baseline temperature, an RFID card or badge provides reliable identification of an employee. As such, a badge scanner 320 may be adapted for use with the with temperature monitor 100 to identify the employee. In another alternative embodiment, a keyboard 310 or other input means may be used in lieu of a touch screen display. The keyboard 310 may be used to identify the employee, or for providing responses to a survey and/or screening questions in lieu of a touch screen display. Additionally, a label printer 220 may be attached to indicate access for the employee.

Figure 4A:
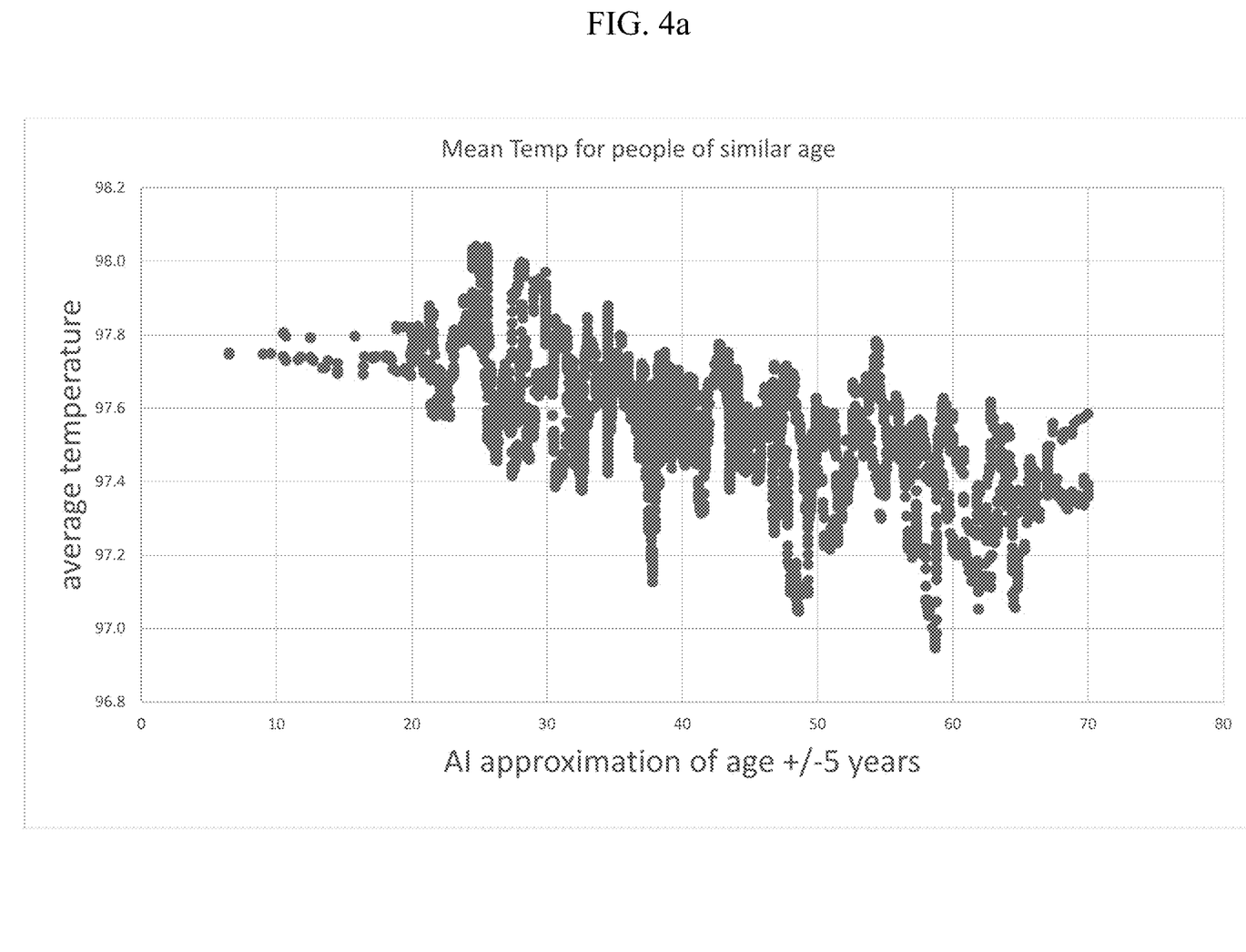
FIG. 4a is a graph showing average baseline temperatures based on ages of persons.

Referring to FIG. 4a, shown is a graph comparing the average temperature of non-febrile persons with respect to their approximate age. A sample size of approximately 6000 persons of varying age and taken at varying times of day was used. To determine the age, an approximation was determined using the facial recognition software with a likely range of error of +/−5 years of age. As depicted in FIG. 4a, as the approximate age of a person increases, their average baseline temperature decreased. For those persons between ages 20-30, the approximate median baseline temperature is 97.8 F degrees. However, as shown in FIG. 4a, for those persons between ages 30-40, the approximate median baseline temperature is 97.6 F degrees. For those persons between ages 40-50, the approximate median baseline temperature is 97.4 F, and the approximate median temperature continues to trend downward for those older in age such that those persons between ages 60-70 have an approximate median baseline temperature of 97.2 F.

Understanding these different baseline temperatures for different age groups in the present invention operates to prevent older persons who may have a temperature below the CDC guideline of fever to escape detection despite the likelihood that such persons may have a febrile condition. As other studies have shown, for persons ages 65 years and older, a temperature of 98.6 F is likely indicative a fever.

Furthermore, as confirmed by the sample size, there is a slight, although noticeable change in approximate baseline temperatures for those in the same age group when temperatures are measured in the morning versus in the evening, thereby verifying the conclusion that baseline temperatures of persons are slightly higher when taken in the evening. These results are for a person in a diurnal cycle, and a person in a nocturnal cycle would have reversed results. With respect to the time of day when a temperature measurement is taken for a person, studies have shown that mean temperature for persons varied with measurements taken at 6 AM generally being the lowest and with measurements taken between 4 to 6 PM generally being the highest.

Figure 4B:
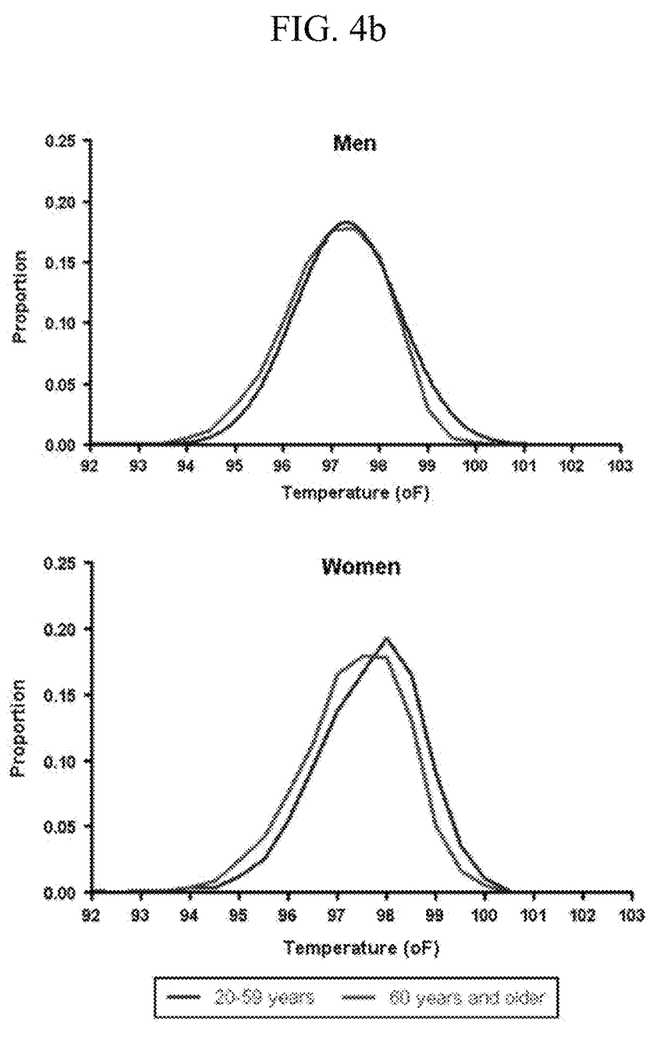
FIG. 4b is a graph showing average baseline temperatures for men and women of different age groups.

Referring to FIG. 4b, the graph shows that for certain age groups, the baseline temperature between genders differ as women during ovulation and menstruation may maintain a slightly higher body temperature due to a spike of progesterone. This is further supported by results that show the while the baseline temperature of between men and women are similar in older persons, younger women have higher baseline temperature than younger men.

In an exemplary embodiment, the temperature monitor 100 obtains a more accurate baseline to determine a febrile condition using the above factors, but any other identifiable factors affecting a person's baseline temperature may also be used.

Figure 5:
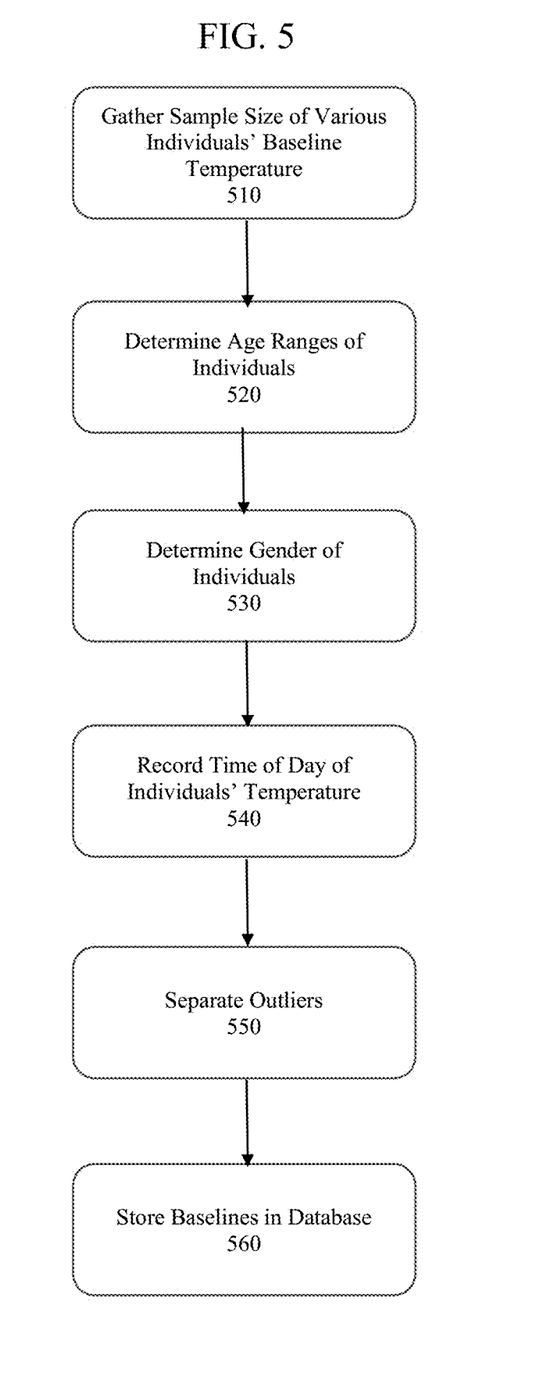
FIG. 5 is a flow chart detailing a novel method of improving the accuracy of determining baseline temperatures for febrile persons in accordance with the present invention.

Referring to FIG. 5, a flow chart of populating and gathering the database of the necessary baseline temperatures in the exemplary embodiment is depicted. In step 510, a statistically significant sample size is collected of various persons to populate the database. In one example, placing a data gathering kiosk in location such as a stadium, an airport, or any other mass transit point allows for a rapid collection of samples from a diverse range of persons. Accuracy could potentially be improved if each person in the sample size also provided their age, gender and other personal information. However, if the sample persons do not enter or provide their age or sex, the gathering process may rely on facial recognition software to estimate an approximate age and likely gender. In steps 520 and 530, the samples collected of various persons' baseline temperatures are associated with age ranges and gender of the persons, either provided by each person or by facial recognition software. In step 540, these samples collected of various persons' baseline temperatures are further correlated with the time of day each sample was taken. Despite a general uniformity in baseline temperature data within age groups, sex, and time of day, some outliers may be identified. Outliers may be averaged into the larger sample pool of their respective ages and/or sex. However, outliers may also be discarded from the final sample size.

In another embodiment, where a specific person's details are known to the data gathering kiosk and temperature system, an individualized baseline temperature may be stored for that specific person. In situations where a known person has a baseline temperature that would otherwise be considered an outlier, multiple recoded samples of baseline temperatures for that specific person may be stored for future individualized determination of a febrile condition for that specific person in step 550. Finally, for all persons in the sample size, individual baseline temperatures and their associated characteristic information are stored in a database 560. The database may be stored in memory on the temperature monitor, on a local server, on a cloud-based server, or on any other form accessible by the temperature monitor.

Figure 6:
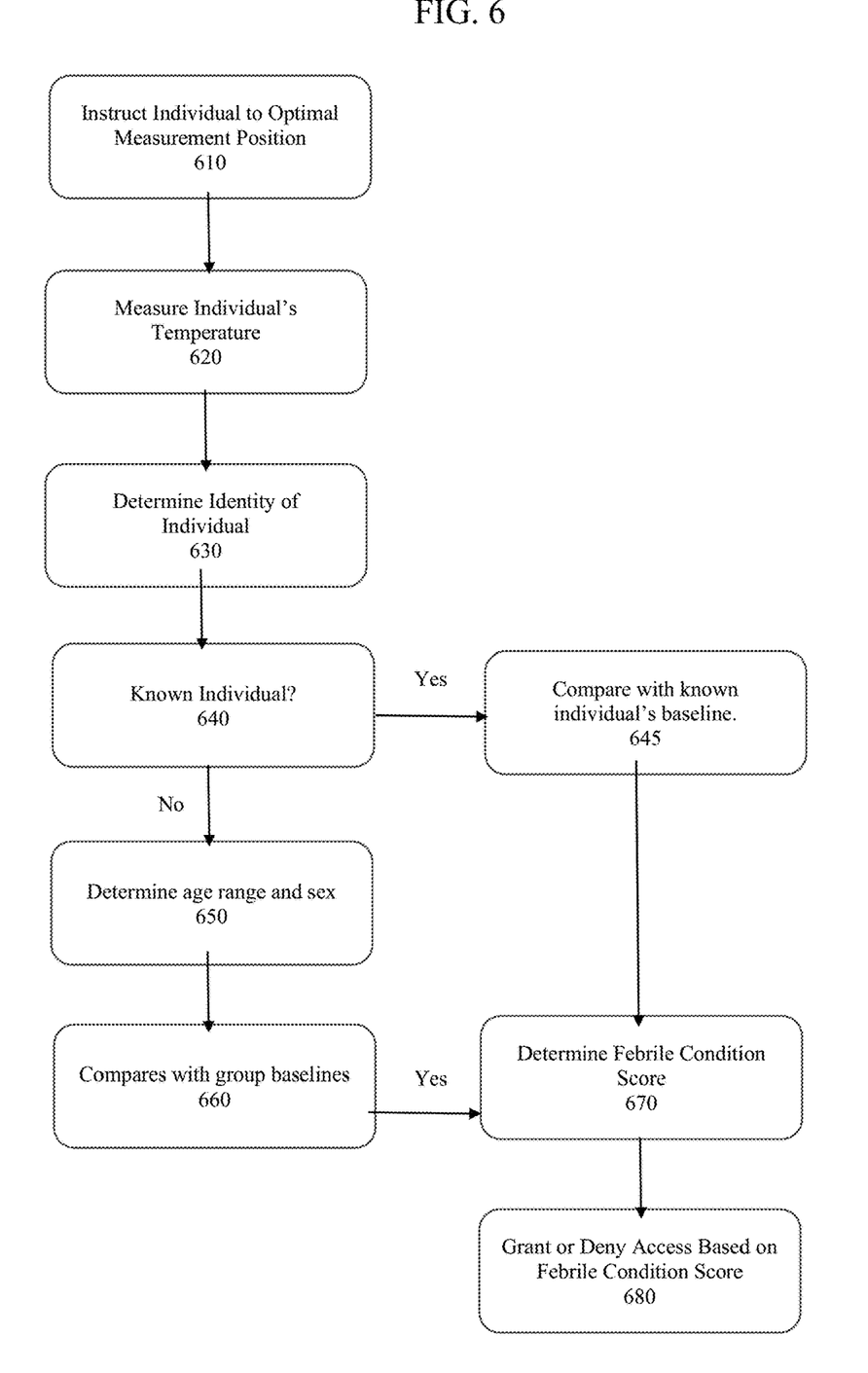
FIG. 6 is a flow chart detailing an exemplary method of accurately determining febrile conditions in persons having different baseline temperatures in accordance with the present invention.

Referring to FIG. 6, a flow chart depicting an exemplary method of accurately determining febrile conditions in persons having different baseline temperatures is shown. When a person approaches a temperature monitor kiosk, preferably located at an ingress, instructions are displayed to guide the person to the optimal measurement position 610. This may be done by text instruction or by a positional overlay. A positional overlay typically includes an outline of a person's head and instructs the person to position his or her head entirely within the outline. Alternatively, an AI facial detector may be used along with or instead of the positional overlay. Similar to the positional overlay, the AI facial detector assists positioning of the person's head. Additional instructions may be given to the person if the temperature sensor is unable to detect the person from the ambient environment.

In step 620, the person's temperature is measured using an infrared thermometer. preferably an FDA Class II cleared thermometer. Optimally, the temperature sensor is an FDA approved non-contact infrared thermometers, as the quality and accuracy of the temperature sensor significantly affects the determination of a febrile condition. In step 630, the identity of the person is determined. This may be done by facial recognition, manual login, RFID card, badge or any other means of identifying persons. In one embodiment determining identity refers to identify the exact identity of the person. This may be done by a user login, an employee badge or other identifier, an RFID card, facial recognition comparison with facial data of known persons, or any other method known in the art.

In step 640, the system determines if the person is known. If the person is one recognized by the system, that person is a known person. As such, in step 645 the known person may be compared with stored baseline temperatures for that specific person to determine uniquely his or her current measured temperature to his or her respective baseline temperatures. Based on his or her respective baseline temperatures, in step 670 a febrile condition score may be determined. In lieu of a full diagnosis, this score is used to determine next steps on whether additional data from the person is needed to determine a febrile condition or whether access should be granted or denied.

In the exemplary embodiment, if during steps 630 and 640, the person is determined to be an unknown person or if no specific baseline temperature data exists for that person, step 650 determines the age, or approximate age and gender of the person. This may be performed by a facial recognition process. For example, U.S. Pat. No. 8,582,807, which is hereby incorporated by reference for all purposes, provides disclosure on generating a baseline gender model and an age estimation model. Numerous other models for determine gender and age from facial recognition exist in the art as the human face provides prior perceptible information about one's age, gender, identity, ethnicity, and mood. Once the unknown person's age and/or gender is determined, in step 660 the measured temperature of that person is compared with group baseline temperatures for persons within the same age range and same gender. Additionally, the comparison may be further refined based on the time of day the measured temperature was taken. Based on the respective baseline temperatures for his or her age and/or gender, in step 670 a febrile condition score may be determined. In lieu of a full diagnosis, this score is used to determine next steps on whether additional data from the person is needed to determine a febrile condition or whether access should be granted or denied in step 680.

In another exemplary embodiment, additional screening tests may be combined to further increase the accuracy to eliminate false positives or false negatives. Two of three methods are typically used by facilities to economize a person's time and expense. They can be typically chosen from the following: 1) setting the temperature screening baseline on the higher side of a person's normal temperature (e.g., elevated temperature; 2) survey screening that the CDC contends is useful (e.g., Do you feel sick; have you been to a [insert high contagion area]); and 3) providing a saliva-based test (e.g., COVID-19 test). However, these three methods have varying time and costs. The first method of temperature screening is typically the fastest and most economical at an average rate of 5 cents per scan for highly trafficked areas. The second method of survey screening is slightly slower and more expensive. Finally, the third method of using a saliva based COVID-19 test is far more expensive at 5 dollars per self-test.

To further improve accuracy, along with step 670 of determining a febrile condition score, the temperature screening described herein may be combined with survey screening or combined with saliva testing. Although this increases the screening/clearance time for persons or employees, the additional methods increase true positive results. Furthermore, in the case of adding saliva self-testing, the accuracy of the temperature screening in addition to saliva self-testing would likely increase confidence level of the results to 95% and can still be performed in a short period. Such features can be added to kiosks to enhance contagion screening. For example, if step 670 determines a likelihood of a febrile condition, a kit may be provided by the screening kiosk to the person such that a nasal swab or saliva test may be administered.

The invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

The invention claimed is:

1. A system for detecting a presence of a febrile condition, the system comprising:
    a processor;
        a camera module for capturing an image of a user;
    a wireless temperature sensor configured to measure a temperature of the user; and
    a display screen;
    wherein the processor is configured to perform steps comprising:
        causing the image of the user to be provided to the display screen;
        causing a positional overlay in an outline of a human head to be presented on the display screen for guiding the user to the wireless temperature sensor, wherein the positional overlay instructs the user to adjust position until the entirety of the user's face is within the positional overlay;
        determining an age category of the user based on a captured image of the user;
        determining a gender of the user based on said captured image of the user;
        comparing the temperature of the user with a pre-stored baseline temperature based on the age category of the user, the gender of the user, and a time of day the temperature of the user was taken to determine if the user has a febrile condition in real time;
        wherein said age category of the user is an age range comprised of 10 years;
        and wherein said pre-stored baseline temperature based on the age category of the user is between 96.9° F. and 98.1 F.

2. The system of claim 1, further comprising an RFID scanner configured to detect an RFID card identifying the user.

3. The system of claim 1, further comprising a code reader configured to detect a code identifying the user.

4. The system of claim 1, further comprising a test kit for secondary screening.

5. A method of detecting a presence of a febrile condition, the method comprising:
- capturing an image of a user using a camera;
- displaying the image of the user on a display coupled to the camera; guiding the user via a positional overlay in an outline of a human head to a wireless temperature sensor, wherein the positional overlay instructs the user to adjust position until the entirety of the user's face is within the positional overlay;
- measuring a temperature of the user by the wireless temperature sensor;
- determining an age category of the user based on a captured image of the user;
- determining a gender of the user based on said captured image of the user;
- comparing the temperature of the user with a pre-stored baseline temperature based on the age category of the user, the gender of the user, and a time of day the temperature of the user was taken to determine if the user has a febrile condition in real time;
- wherein said age category of the user is an age range comprised of 10 years;
- and wherein said pre-stored baseline temperature based on the age category of the user is between 96.9° F. and 98.1° F.

6. The method of claim 5, further comprising identifying the user based on a user identification card.

7. The method of claim 5, further comprising identifying the user based on a user code.

8. The method of claim 5, further comprising scanning the user's face for hypoxia based on a color of the user's skin.

9. The method of claim 5, further comprising directing the user to a secondary screening upon determining the presence of a febrile condition of the user.

10. The method of claim 9, wherein directing the user to the secondary screening comprises directing the user to take one of a nasal swab or saliva test.

11. A system for detecting a presence of a febrile condition, the system comprising:
- a processor;
- a non-volatile memory storing facial recognition software;
- a camera module for capturing an image of a user;
- a wireless temperature sensor configured to measure a temperature of the user;
- a display screen;
- wherein the processor is configured to perform steps comprising: causing the image of the user to be provided to the display screen;
- causing a head shaped positional overlay to be presented on the display screen for guiding the user to the wireless temperature sensor, wherein the positional overlay instructs the user to adjust position until the entirety of the user's face is within the positional overlay;
- calculating an approximate age of the user based on the facial recognition software;
- determining an age category of the user based on a captured image of the user;
- comparing the temperature of the user with a pre-stored baseline temperature based on the age category of the user to determine if the user has a febrile condition in real time;
- wherein said age category of the user is an age range of 20 to 59 years or 60 years and older; and
- wherein said pre-stored baseline temperature based on the age category of the user is between 93° F. and 101° F.

12. The system of claim 11, further comprising a test kit for secondary screening.

13. A method of detecting a presence of a febrile condition, the method comprising:
- capturing an image of a user using a camera;
- displaying the image of the user on a display coupled to the camera; guiding the user via a face shaped positional overlay to a wireless temperature sensor, wherein the positional overlay instructs the user to adjust position until the entirety of the user's face is within the positional overlay;
- calculating an approximate age of the user based on facial recognition software;
- determining an age category of the user based on the image of the user;
- determining a gender of the user based on the facial recognition software;
- determining a time of day said image of the user was captured;
- measuring a temperature of the user using the wireless temperature sensor;
- comparing the temperature of the user with a pre-stored baseline temperature based on the age category of the user, the gender of the user, and a time of day the temperature of the user was measured to determine if the user has a febrile condition in real time;
- wherein said age category of the user is an age range of 20 to 59 years or 60 years and older;
- and wherein said pre-stored baseline temperature based on the age category of the user is between 93° F. and 101° F.

14. The method of claim 13, further comprising scanning for hypoxia based on a color of the user's skin.

15. The method of claim 13, further comprising directing the user to a secondary screening upon the determining of a febrile condition of the user.

16. The method of claim 15, wherein directing the user to the secondary screening comprises directing the user to take one of a nasal swab or saliva test.

\* \* \* \* \*